US010410092B1

(12) United States Patent
Chen et al.

(10) Patent No.: US 10,410,092 B1
(45) Date of Patent: Sep. 10, 2019

(54) AUTOMATED CLASSIFICATION OF ROCK TYPES AND ANALYST-CENTRIC VISUALIZATIONS—FRONT END

(71) Applicant: HRL Laboratories, LLC, Malibu, CA (US)

(72) Inventors: Yang Chen, Malibu, CA (US); Deepak Khosla, Camarillo, CA (US); Fredy Monterroza, Malibu, CA (US); Ryan M. Uhlenbrock, Calabasas, CA (US)

(73) Assignee: HRL Laboratories, LLC, Malibu, CA (US)

( * ) Notice: Subject to any disclaimer, the term of this patent is extended or adjusted under 35 U.S.C. 154(b) by 144 days.

(21) Appl. No.: 15/380,039

(22) Filed: Dec. 15, 2016

Related U.S. Application Data

(60) Provisional application No. 62/268,498, filed on Dec. 16, 2015, provisional application No. 62/333,114, filed on May 6, 2016.

(51) Int. Cl.
*G06K 9/62* (2006.01)
*G06K 9/46* (2006.01)
*G01N 33/24* (2006.01)

(52) U.S. Cl.
CPC .......... *G06K 9/6267* (2013.01); *G01N 33/24* (2013.01); *G06K 9/46* (2013.01)

(58) Field of Classification Search
CPC . G06T 2207/20081; G06T 2207/20084; G06T 1/20; G06T 7/11; G06K 9/6267–9/6287; G06K 9/46–9/527; G01N 2223/616; G01N 33/24–2033/248; G06N 3/04–3/049
See application file for complete search history.

(56) References Cited

U.S. PATENT DOCUMENTS

2017/0061249 A1* 3/2017 Estrada .................. G06T 7/344

OTHER PUBLICATIONS

Thomas et al., "Automated lithology extraction from core photographs", first break vol. 29, Jun. 2011, EAGE, cover page and pp. 103-109. (Year: 2011).*

(Continued)

*Primary Examiner* — Brian Werner
(74) *Attorney, Agent, or Firm* — Lewis Roca Rothgerber Christie, LLP

(57) ABSTRACT

A system and method of automated classification of rock types includes: partitioning, by a processing device, an image into partitions; extracting, by the processing device, sub-images from each of the partitions; first-level classifying, by an automated classifier, the sub-images into corresponding first classes; and second-level classifying, by the processing device, the partitions into corresponding second classes by, for each partition of the partitions, selecting a most numerous one of the corresponding first classes of the sub-images extracted from the partition. A method of displaying automated classification results on a display device is provided. The method includes: receiving, by a processing device, an image partitioned into partitions and classified into corresponding classes; and manipulating, by the processing device, the display device to display the image together with visual identification of the partitions and their corresponding classes. The method may include generating a depth-aligned log file of the classifications.

17 Claims, 13 Drawing Sheets
(8 of 13 Drawing Sheet(s) Filed in Color)

(56) References Cited

OTHER PUBLICATIONS

Lepisto et al, "Rock image classification based on k-nearest neighbour voting", IEE Proc.-Vis. Image Signal Process., vol. 153, No. 4, Aug. 2006, pp. 475-482. (Year: 2006).*

Lepisto et al., "Rock Image Classification Using Non-Homogenous Textures and Spectral Imaging", WSCG Short Papers proceedings, WSCG'2003, Feb. 3-7, 2003, Plzen, Czech Republic, 5 pages total. (Year: 2003).*

Cao et al., "Spiking Deep Convolutional Neural Networks for Energy-Efficient Object Recognition", Int J Comput Vis (2015) 113:54-66, Published online: Nov. 23, 2014, pp. 54-66. (Year: 2014).*

* cited by examiner

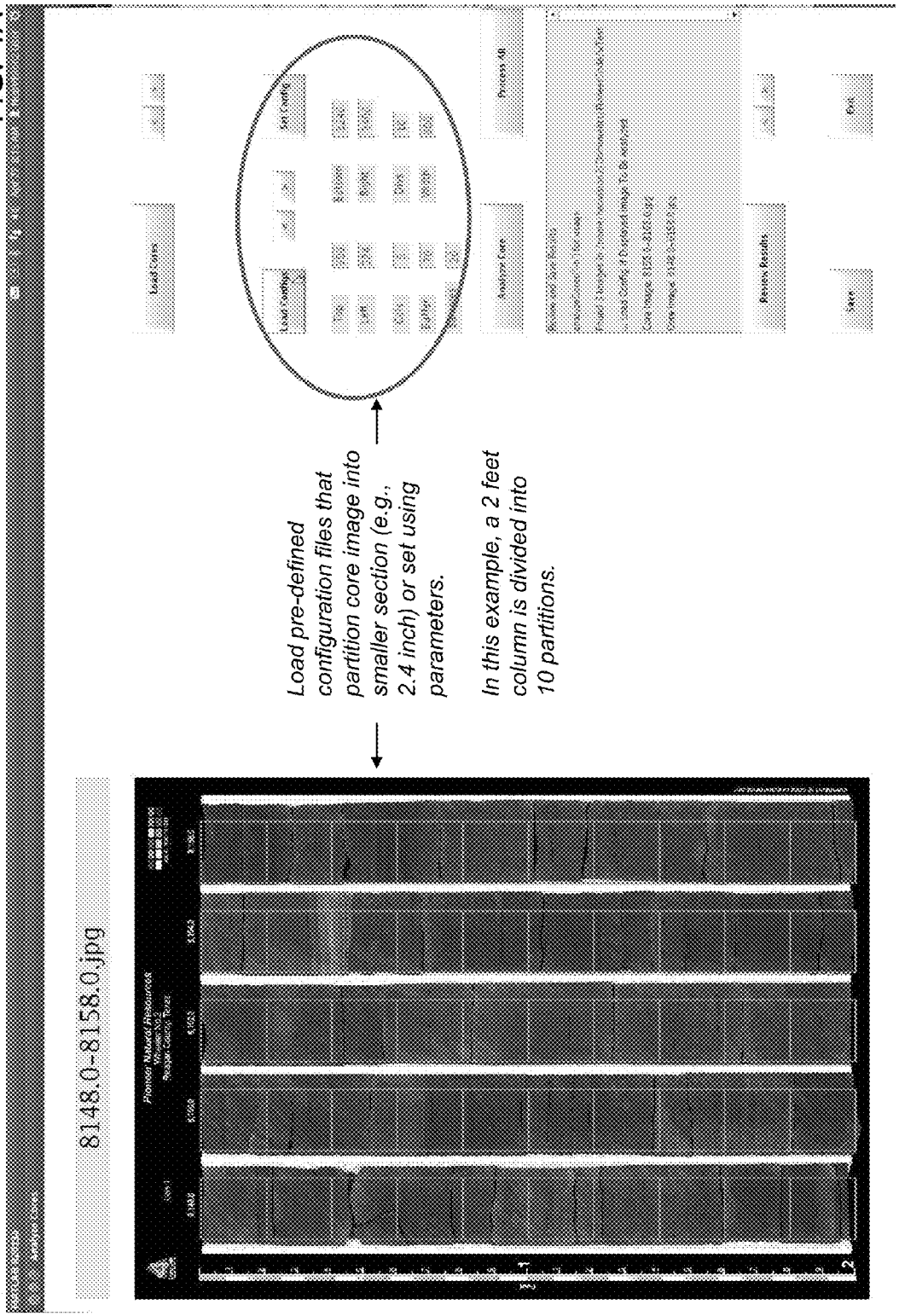

AUTOMATED CLASSIFICATION OF ROCK TYPES AND ANALYST-CENTRIC VISUALIZATIONS—FRONT END

CROSS-REFERENCE TO RELATED APPLICATIONS

This application claims priority to and the benefit of U.S. Provisional Appl. No. 62/268,498, filed Dec. 16, 2015, and U.S. Provisional Appl. No. 62/333,114, filed May 6, 2016, the entire contents of all of which are incorporated herein by reference. This application is related to U.S. application Ser. No. 15/380,120, filed Dec. 15, 2016, titled "AUTOMATED CLASSIFICATION OF IMAGES USING DEEP LEARNING—BACK END", the entire contents of which is incorporated herein by reference.

BACKGROUND

1. Field

Aspects of embodiments of the present invention relate to automated classification of rock types and analyst-centric visualizations.

2. Description of Related Art

Rock formations, especially images of rock formations (such as photographs), are good examples of inputs for a classification problem. Rock classification, and more specifically automated rock classification, has been a long-standing topic of interest. However, existing automated tools, such as neural networks, can only assist with the classifying; much of the rock classification effort (such as feature selection) still needs to be done by scientists and other experts in the field.

SUMMARY

Aspects of embodiments of the present invention are directed to an image classification algorithm and core analysis system and tool that can characterize and classify rock types from various photos (e.g., core photos, computed tomography (CT) scan photos, etc.) rapidly and accurately without requiring feature pre-selection and at a rate not achievable with human intervention. Further aspects provide for confidences in classification and analyst-centric geological visualizations for the end-user (e.g., geologist or petrophysicist). Still further aspects provide for methods of classifying and identifying lithofacies from wellbore core and other types of photos.

Aspects of embodiments of the present invention are directed to classifying an image by using all of the information in the image automatically and without pre-deciding or selecting what subset of features to consider or other acts requiring human intervention. Further aspects are generalizable to any photo classification problem regardless of the well or the domain. By way of non-limiting example, aspects of embodiments of the present invention are applicable to core photos, CT scans, thin sections, well-log converted images (e.g., resistivity), etc.

According to an embodiment of the present invention, a method of automated classification is provided. The method includes: partitioning, by a processing device, an image into partitions; extracting, by the processing device, sub-images from each of the partitions; first-level classifying, by an automated classifier, the sub-images into corresponding first classes; and second-level classifying, by the processing device, the partitions into corresponding second classes by, for each partition of the partitions, selecting a most numerous one of the corresponding first classes of the sub-images extracted from the partition.

The method may further include displaying, on a display device, visual results of the automated classification, the visual results including the image together with visual identification of the partitions and their corresponding second classes.

The image may be of a rock core sample, the partitions may be of different portions of the core sample, and each of the first and second classes may include different rock strata.

The method may further include displaying, on a display device, visual results of the automated classification, the visual results including the image together with visual identification of the partitions and their corresponding second classes distinguishing the different rock strata.

The method may further include identifying, by the processing device, artifacts in the partitions. The extracting of the sub-images may include excluding any of the sub-images that contain any of the artifacts.

The automated classifier may be a convolutional neural network.

The partitioning of the image may include dividing the image into nonoverlapping said partitions.

The sub-images may be fixed size.

The extracting of the sub-images may include, for each partition of the partitions, dividing the partition into a maximum number of nonoverlapping said sub-images.

The extracting of the sub-images may include, for each partition of the partitions, uniformly randomly sampling the partition to select the sub-images of the partition.

The extracting of the sub-images may include, for each partition of the partitions, uniformly gridding the partition into the sub-images with overlap in horizontal and vertical directions between the sub-images of the partition.

Overlapping ones of the sub-images may overlap in the horizontal or vertical direction by about a set amount.

The set amount may be 50%.

The selecting of the most numerous one of the corresponding first classes of the sub-images extracted from the partition may further include assigning a confidence score to the selection based on a distribution of the corresponding first classes of the sub-images extracted from the partition.

The method may further include displaying, on a display device, visual results of the automated classification, the visual results including the image together with visual identification of the partitions and their corresponding second classes and confidence scores.

According to another embodiment of the present invention, a method of generating a depth-aligned log file is provided. The method includes: receiving, by a processing device, an image partitioned into partitions and classified into corresponding classes of a plurality of classes; generating the depth-aligned log file, the depth-aligned log file including a plurality of lines, each line of the plurality of lines corresponding to one of the partitions, each line including a depth of the corresponding partition and a classification of the corresponding partition; and outputting, by the processing device, the depth-aligned log file.

Each line of the depth-aligned log file may further include a confidence of the classification.

Each line of the depth-aligned log file may further include a confidence of classification for each of the classes.

The corresponding classes of the partitions may include a breakdown of each of the rock strata in each of the partitions, and the confidence classifications for each of the classes correspond to the confidence of classifying the corresponding partition as a corresponding one of the rock strata.

According to yet another embodiment of the present invention, a system for automated classification is provided. The system includes a central processing unit, an automated classifier configured to run on the central processing unit, and a non-transitory physical medium. The medium has instructions stored thereon that, when executed by the central processing unit, causes the central processing unit to: partition an image into partitions; extract sub-images from each of the partitions; use the automated classier to perform first-level classification of the sub-images into corresponding first classes; and perform second-level classifying of the partitions into corresponding second classes by, for each partition of the partitions, selecting a most numerous one of the corresponding first classes of the sub-images extracted from the partition.

The automated classifier may be configured to run on a central processing unit.

The automated classifier may be configured to run on a neuromorphic chip.

The medium may further have instructions stored thereon that, when executed by the central processing unit, cause the central processing unit to: identify one or more artifacts in the partitions, wherein the instructions that, when executed by the central processing unit, cause the central processing unit to extract the sub-images from each of the partitions include instructions that cause the central processing unit to exclude any of the sub-images that contain any of the artifacts.

The medium may further have instructions stored thereon that, when executed by the central processing unit, causes the central processing unit to: display, on a display device, visual results of the classification, the visual results including the image together with visual identification of the partitions and their corresponding second classes.

According to one embodiment of the present invention, a non-volatile computer readable medium having instructions stored thereon that, when executed by a central processing unit, cause the central processing unit to: receive an image; partition the image into a plurality of partitions; extract sub-images from each of the partitions; first-level classify, by an automated classifier, the sub-images into corresponding first classes; and second-level classify the partitions into second classes by, for each partition of the partitions, selecting a most numerous one of the corresponding first classes of the sub-images extracted from the partition.

The non-volatile computer readable medium may further have instructions stored thereon that, when executed by the central processing unit, cause the central processing unit to display, on a display device, visual results of the automated classification, the visual results including the image together with visual identification of the partitions and their corresponding second classes.

The image may be of a rock core sample, the partitions may be of different portions of the core sample, and each of the first and second classes may identify different rock strata.

The above and other embodiments of the present invention provide for automated classification, confidence scores, and visualization of rock types from photos. This may allow, for example, a project geologist or petrophysicist, regardless of experience or expertise, to help identify key lithofacies for further investigation of "sweet spots" in a rapid timeframe. Embodiments of the present invention have extensive applications within the niche of descriptive geoscience, a highly observation-based science that drives upstream energy sector and markets in the U.S. and worldwide. For example, embodiments of the present invention may be directed to the automotive industry (e.g., automated driving, active safety, robotics), aerospace industry (e.g., intelligence, surveillance, and reconnaissance (ISR), border security, unmanned systems, robotics), or other industries, such as geology, petrophysics, geoscience, mining, oil, and natural gas industries (e.g., optimize production).

Further embodiments of the present invention provide for automatically using image data as input and for subsequent automated classification. Still further embodiments provide for core classification. Aspects of these and other embodiments of the present invention are directed to applications and evaluation of images (such as photos) to the classification problem.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The accompanying drawings, together with the specification, illustrate example embodiments of the present invention. These drawings, together with the description, serve to disclose aspects and principles of the present invention.

FIG. 4A illustrates an example partition generation via pre-defined or user-defined configurations according to an embodiment of the present invention.

DETAILED DESCRIPTION

Figure 1:
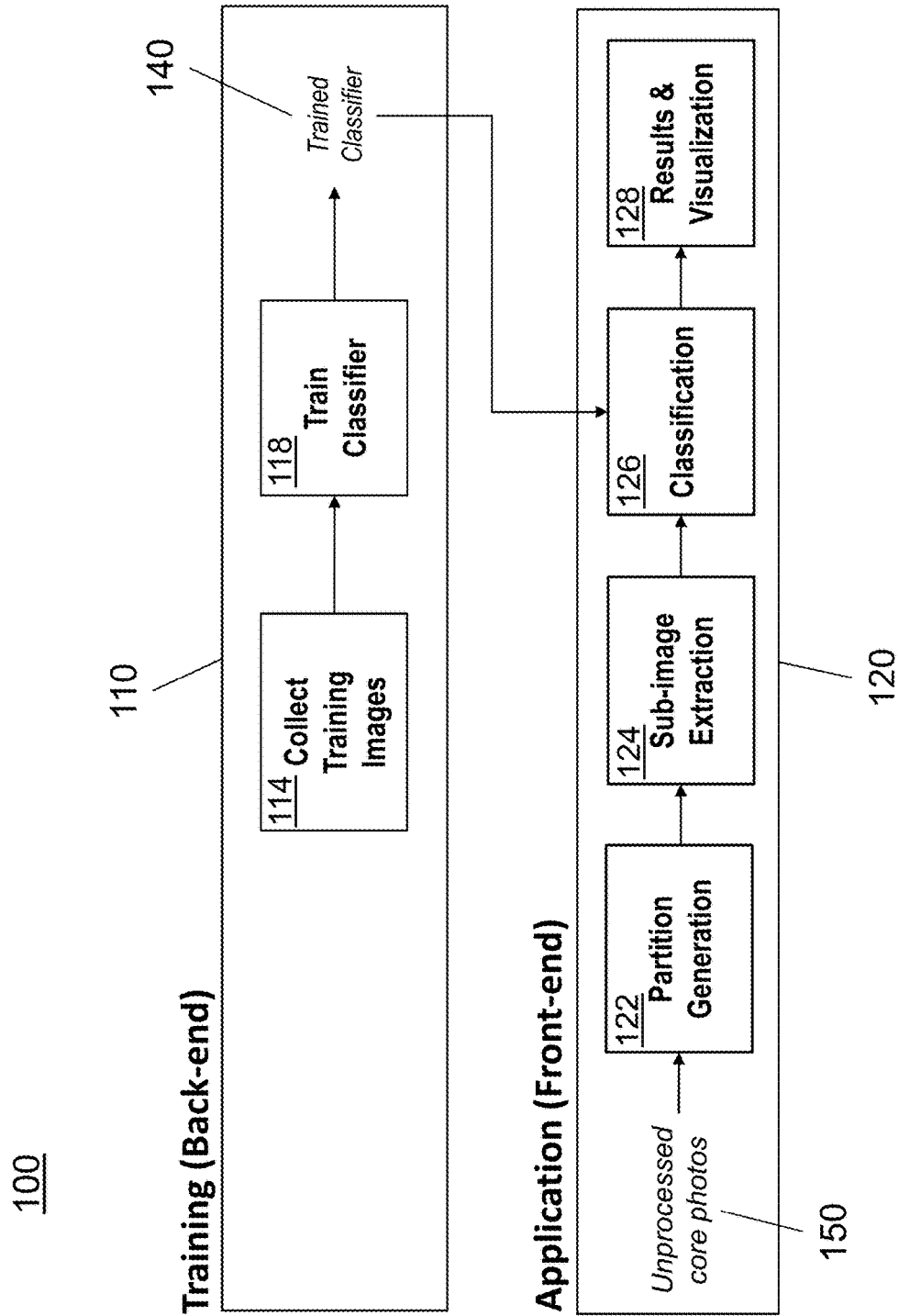
FIG. 1 is a block diagram of a core analysis system, including back-end training and front-end application components, according to an embodiment of the present invention.

Example embodiments of the present invention will now be described with reference to the accompanying drawings. The present invention, however, may be embodied in various different forms, and should not be construed as being limited to the illustrated embodiments herein. In the drawings, the same or similar reference numerals refer to the same or similar elements throughout. As used herein, the term "substantially," "about," and similar terms are used as terms of approximation and not as terms of degree, and are intended to account for the inherent deviations in measured or calculated values that would be recognized by those of ordinary skill in the art. Herein, the use of the term "may," when describing embodiments of the present invention, refers to "one or more embodiments of the present invention." In addition, the use of alternative language, such as "or," when describing embodiments of the present invention, refers to "one or more embodiments of the present invention" for each corresponding item listed.

Embodiments of the present invention may be implemented using a processor, or central processing unit (CPU), or processing device. The processor, CPU, and/or processing device include electronic or electric devices and/or any other relevant devices or components according to embodiments of the present invention described herein may be implemented utilizing any suitable hardware, firmware (e.g. an application-specific integrated circuit (ASIC)), software, or a combination of software, firmware, and hardware. For example, a processing device may include a central processing unit coupled to memory, where the central processing unit is configured to execute instructions stored in the memory. For example, in one embodiment of the present invention, a processing device may include a neuromorphic integrated circuit or neuromorphic chip is used to implement a embodiments of the present invention (see, e.g., the circuit described in U.S. patent application Ser. No. 15/043,478 "Spike Domain Convolution Circuit," the entire disclosure of which is incorporated by reference herein). For example, the various components of these processing devices may be formed on one integrated circuit (IC) chip or on separate IC chips. Further, the various components of these devices may be implemented, for example, on a flexible printed circuit film, a tape carrier package (TCP), a printed circuit board (PCB), or formed on one substrate. In addition, the various components of these devices may be a process or thread, running on one or more processors or CPUs, in one or more computing devices, executing computer program instructions and interacting with other system components for performing the various functionalities described herein.

The computer program instructions may be stored in a memory that may be implemented in a computing device using a standard memory device, such as, for example, a random access memory (RAM). The computer program instructions may also be stored in other non-transitory computer readable media such as, for example, a CD-ROM, DVD, flash drive, or the like. In addition, a person of skill in the art should recognize that the functionality of various computing devices may be combined or integrated into a single computing device, or the functionality of a particular computing device may be distributed across one or more other computing devices without departing from the spirit and scope of the present invention.

Embodiments of the present invention are directed to classification systems, such as core analysis classification systems, and their corresponding components, such as back-end training and front-end application components. By way of example, core analysis systems may be directed to rock classification, providing an automated system for the classification of rocks from, for example, unprocessed photographs (photos) of the rocks to different results and visualizations useful for end users.

FIG. 1 is a conceptual diagram of an example core analysis system 100, including back-end training 110 and the Core Classification System—Front End 120 components, according to an embodiment of the present invention. In some embodiments, the back-end training 110 and the Core Classification System—Front End 120 may be implemented by the same computer system, such as a general purpose computer including a processor and memory, as described in more detail below with respect to FIG. 11. In other embodiments of the present invention, the back-end training 110 and the Core Classification System—Front End are implemented by different computer systems (e.g., one computer system implements back end training 110 to generate a trained classifier 140 that is provided to another computer system implementing the Core Classification System—Front End 120). As discussed above, the computer system that implements the back end training 110 may include a neuromorphic chip that is trained by setting the weights of connections within the chip, and the computer system that implements the Core Classification System—Front End 120 may include a neuromorphic chip that is configured to implement a classifier (e.g., in accordance with weights set by the back-end training 110).

Referring to FIG. 1, the core analysis system 100 includes back-end training components 110 and the Core Classification System—Front End 120. The training back-end 110 may encapsulate a training process to produce a trained model or classifier, while the Core Classification System—Front End 120 may use the trained model to classify images and to generate results.

During the training (back-end) phase 110, several steps may be performed, such as collecting training images 114 for training the model and training the model 118 to generate a trained classifier 140. Within the Core Classification System—Front End 120, further steps may be performed, such as partition generation 122 on unprocessed core photos 150 (e.g., rock formation images), sub-image extraction 124 on the generated partitions to create input for a classifier (such as the trained classifier 140), performing the classification 126 on the extracted sub-images using the classifier 140, and displaying results and other visualizations 128 of outputs from the classification.

Figure 2:
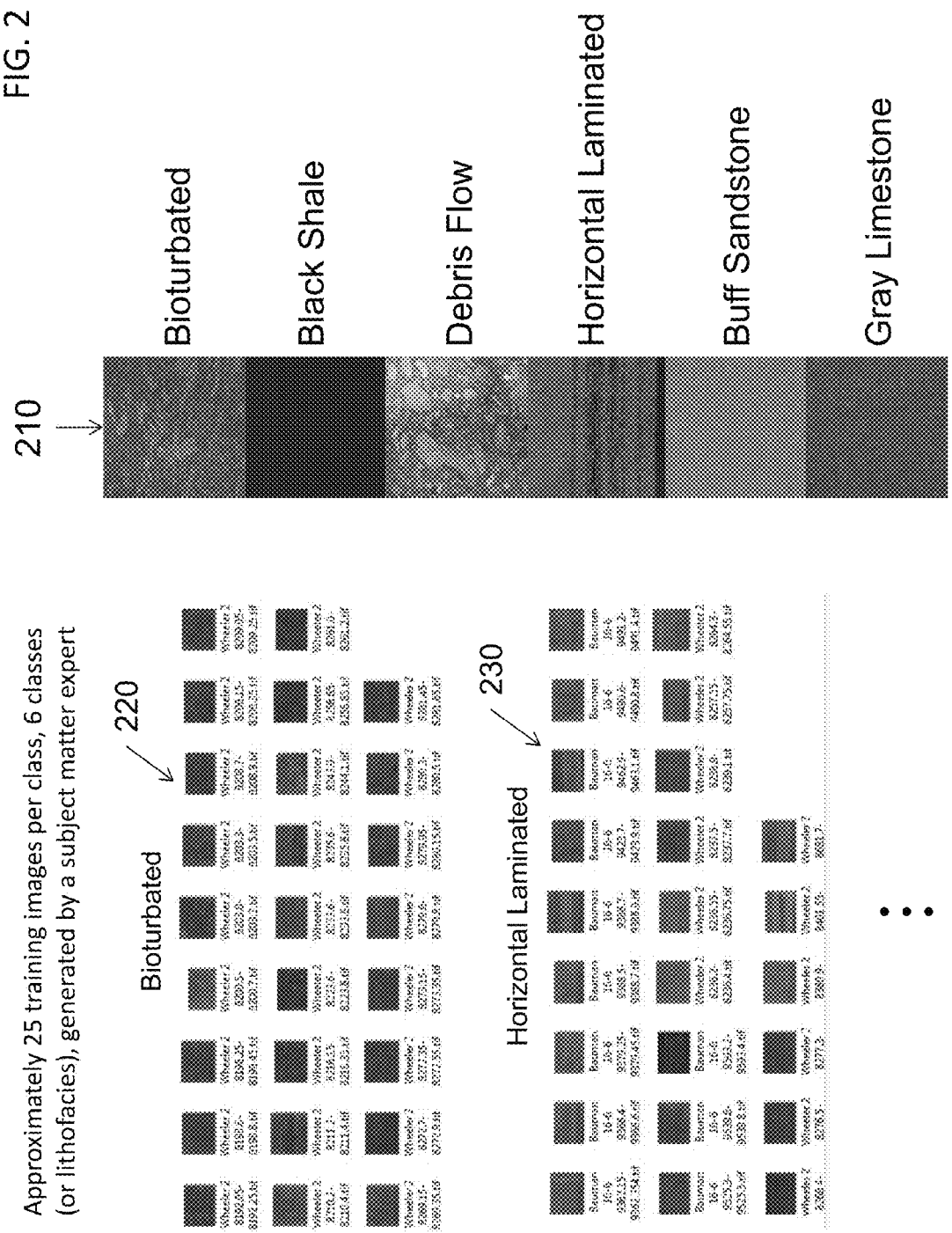
FIG. 2 is an example set of training images for training a classifier to do rock classification according to an embodiment of the present invention.

FIG. 2 is an example set of training images for training a classifier to do rock classification according to an embodiment of the present invention.

During training, the model or classifier may benefit from a training set of images that contains samples representative of each class under a variety of conditions. This set may be collected, for example, by a human annotator (subject matter expert) who creates a reference dictionary of lithofacies images representing a manual descriptive workflow.

Referring to FIG. 2, for ease of description, there are a collection of approximately 25 images for each of two classes of lithofacies (Bioturbated 220 and Horizontal Laminated 230) out of a potential of 6 classes 210 (further including Black Shale, Debris Flow, Buff Sandstone, and Gray Limestone) present in a core sample.

Figure 3:
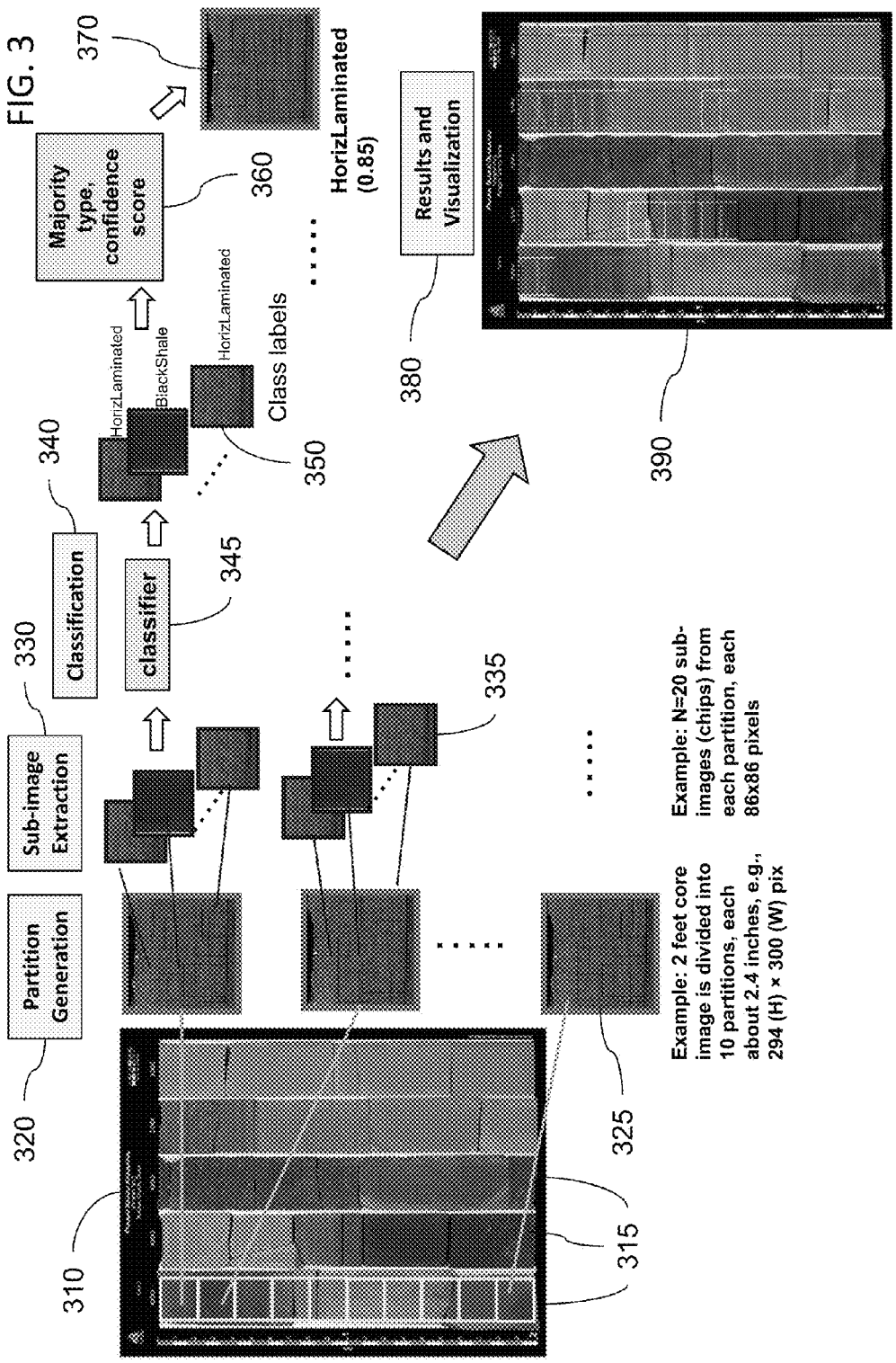
FIG. 3 is a block diagram illustrating example front-end (application) component steps and data flow according to an embodiment of the present invention.

FIG. 3 is a block diagram illustrating example front-end (application) component steps and data flow according to an embodiment of the present invention.

Referring to FIG. 3, the application front-end 120 may automatically process input images and produce an output 390, such as a file, containing classifications as well as a visual depiction of the results. In further detail, an input image 310 may include a single core sample of ten feet arranged vertically in two-foot sections 315. The image 310 may undergo partition generation 320, where each of the two-foot sections 315 may be partitioned into ten partitions 325, each roughly 0.2 foot (2.4 inch) square. For example, each partition 325 may be 294 pixels high (vertical) by 300 pixels wide (horizontal). Sub-image extraction 330 may be performed on each of the partitions 325 to generate sub-images (chips) 335. These numbers (and other similar numbers disclosed herein) are only examples and the present invention is not thereto limited.

For example, each partition 325 may have N=20 sub images 335 extracted from it, where each sub image 335 is an 86 pixel by 86 pixel sub-image of the partition 325. The sub images 335 may have a fixed size and may overlap each other (for example, partially overlap, such as share an edge or corner portion). Further, the sub images 335 may be randomly distributed (e.g., in accordance with a uniform distribution) in the partition 325. The sub images 335 may undergo classification (e.g., first-level classification) 340 using a classifier 345 (e.g., a convolutional neural network (CNN) or other automated classifier, for example as described in "AUTOMATED CLASSIFICATION OF IMAGES USING DEEP LEARNING—BACK END", U.S. application Ser. No. 15/380,120, filed Dec. 15, 2016) that assigns one of a set of classes (or class labels) 350 to each of the sub-images 335. In addition, the assignment of classes 350 to each sub image 335 may include the generation of confidence scores. For instance, a particular partition 325 having 20 sub images 335 may have 17 corresponding classifications 350. Example classifications 350 in the field of rock lithofacies include Horizontal Laminated together with three other classifications (such as Black Shale, Bioturbated, and Debris Flow) for those of the sub images 335 that do not classify as Horizontal Laminated.

After labeling each sub image 335 with a corresponding class 350, the partition 325 itself may be classified (e.g., second-level classification) 360 based on the classifications of its corresponding sub images 335. For example, a majority scheme (e.g., majority vote, majority type) may be used to assign a classification (e.g., Horizontal Laminated) and confidence score (e.g., 0.85 or 85% or 17 out of 20) to a partition 325. The different classifications and confidence scores may be assembled as an output or a set of results 390 and visualized 380 on a display device (e.g., an electronic display device, such as a computer monitor) in an annotated or otherwise visualized form 390, such as color-coded classifications or confidence scores for each of the partitions 325 for each of the sections 315 making up the core image 310. The output 390 may provide the classifications of the different portions of the sample as a function of the distance along the image 310 (e.g., depth of partition along the core sample).

FIG. 4A illustrates an example partition generation (e.g., partition generation 320 in FIG. 3) via pre-defined or user-defined configurations according to an embodiment of the present invention.

According to an embodiment of the present invention, a core photo (e.g., a ten-foot core sample, such as the five 2-foot sections on the left of FIG. 4) is input into the partition generator and divided it into smaller-sized partitions that are suitable for classification (e.g., by classifier 345 of FIG. 3) and of an appropriate size and granularity (e.g., as chosen by an analyst of the classification data and results, or by someone of ordinary skill in the art). The system may load pre-defined configuration files that partition core image into smaller section (e.g., 2.4 inch) or set using parameters. For example, an analyst may require class labels at every 0.2 feet depth. This may be accomplished by sampling a 2 feet image column in 10 partitions (each 0.2 feet or 2.4 inches long). This may be repeated for each column of the core image (e.g., five such columns for each ten feet of core sample, covering the entire depth represented by the core image).

According to an embodiment of the present invention, this may be done by loading one of many pre-defined partitioning configurations or allowing an arbitrary user-defined configuration with desired granularity. An example is shown in FIG. 4A. The system may notify the user if an inappropriate configuration is supplied, e.g., one that does not fit within the known bounds of the core.

Figure 4B:
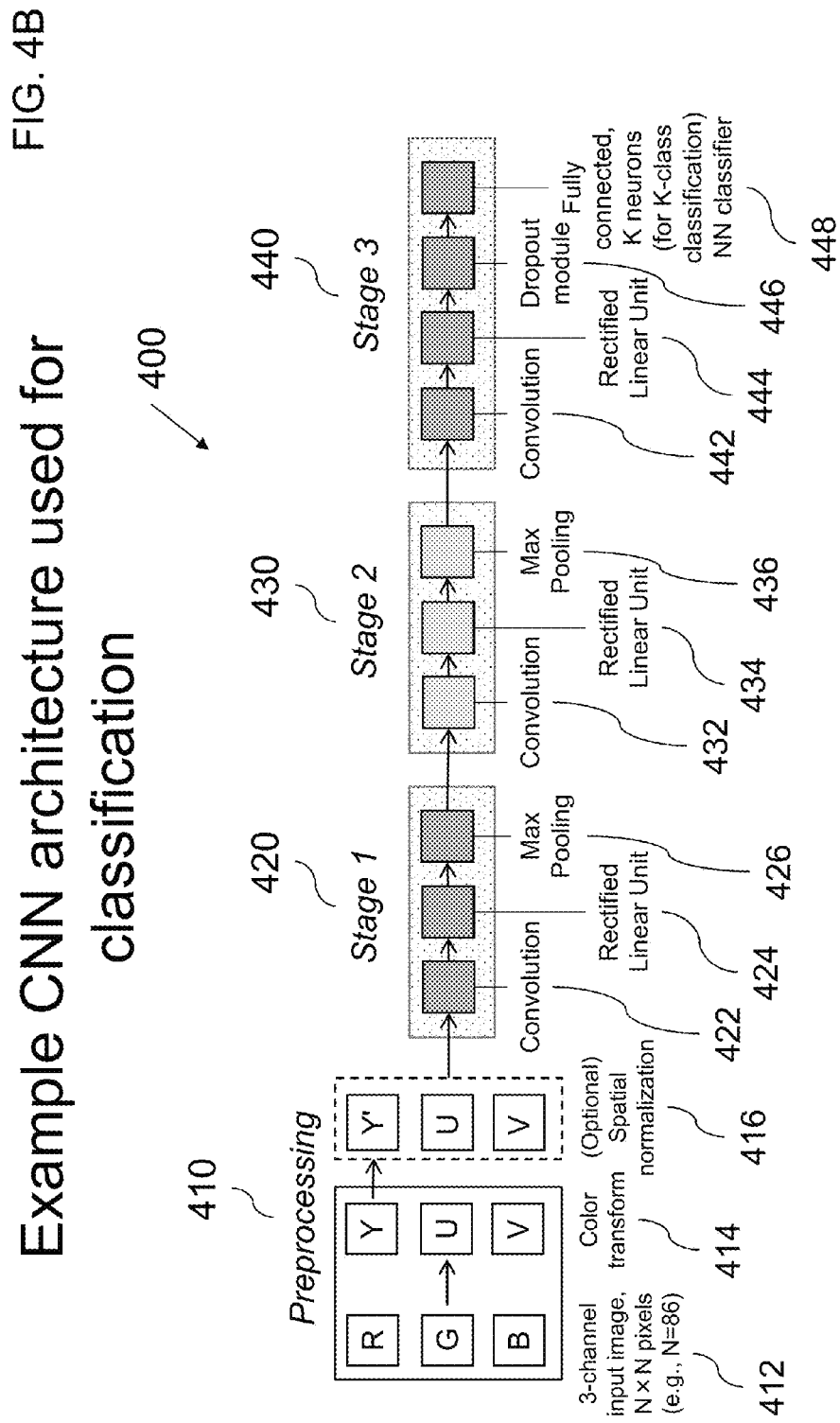
FIG. 4B is a block diagram of an example convolutional neural network (CNN) architecture for image classification according to an embodiment of the present invention.

FIG. 4B is a block diagram of an example convolutional neural network (CNN) architecture for image classification according to an embodiment of the present invention.

A convolutional neural network (CNN) is a supervised deep-learning neural network with multiple layers of similarly structured convolutional feature extraction operations followed by a linear neural network (NN) classifier. CNNs may be used for image recognition through automatic learning of image features. A CNN may include alternating layers of simple and complex computational cells analogous to a mammalian visual cortex. In a CNN, simple cells may perform template matching and complex cells may pool these results to achieve invariance. See, e.g., LeCun, Y., Kavukcuoglu, K., and Farabet, C. (2010), Convolutional Networks and Applications in Vision, *International Symposium on Circuits and Systems* (*ISCAS'*10), IEEE, Paris, 2010, and U.S. patent application Ser. No. 15/043,478 "Spike Domain Convolution Circuit," the entire contents of which are incorporated herein by reference, for further description of CNNs.

For example, a CNN 400 as shown in FIG. 4B may have several 3-layer convolution stages 420, 430 followed by a four layer classifier stage 440 that is a linear Neural Network (NN) with one or more hidden layers. Generally, in a linear neural network, the neurons in one layer perform computations that are linear functions of their inputs (e.g., the form:

$$y_i = \sum_j w_{ij} y_j$$

where $y_i$ is the output of the i-th neuron, $y_j$ is the input from the j-th input neuron, and $w_{ij}$ is the weight associated with the connection from the j-th neuron to the i-th neuron) and supply these computed outputs to a successive layer of neurons, or in the case of the last layer, an output neuron representing the output of the neural network (see, e.g., Basheer, I. A., and M. Hajmeer. "Artificial neural networks: fundamentals, computing, design, and application." *Journal of microbiological methods* 43.1 (2000): 3-31.). Each convolution stage 420, 430 may have three layers: 1) a filter bank layer (Convolution) 422, 432 to simulate simple cells (e.g., using a separate feature map and the convolution operator to identify a particular feature anywhere in the input image for each feature of interest), 2) a non-linearity activation layer (Rectified Linear Unit) 424, 434, and 3) a feature pooling layer (Max Pooling) 426, 436 to simulate complex cells. The entire network may be trained using backpropagation (backward propagation of errors) with stochastic gradient descent (an optimization algorithm, see, e.g., LeCun, Yann A., et al. "Efficient backprop." *Neural networks: Tricks of the trade.* Springer Berlin Heidelberg, 2012. 9-48). Due to its feedforward nature (non-recursive) and uniform computation within each convolution stage, CNNs such as these may be computationally very efficient.

The CNN 400 of FIG. 4B may perform image classification (e.g., lithofacies) from images (e.g., photos) of rock (e.g., wellbore core). Referring to FIG. 4B, a 3-stage CNN 400 (including first stage 420, second stage 430, and third stage 440) may be used, though more stages may be used for a high-dimensional classification application. To prepare the data, a preprocessing module 410 may be used, where input RGB (red green blue) color images may be resized to a canonical size of N×N pixels 212 (such as N=86) regardless of their original aspect ratio.

In other embodiments, the RGB image may be transformed to a YUV color space 414 (where Y represents a luminance or perceived brightness component and UV represents chrominance (color) components). Further, the YUV image may be spatially normalized 416 (e.g., the Y channel may be processed by local subtractive and divisive normalization, such as to a Y'UV color space, where Y' is a luma, radiance, or electronic (voltage) brightness component).

For example, for the N=86 case, the convolution layer (filter bank) 422 of the first stage 420 may have 8 convolution filter kernels (e.g., corresponding to 8 different features). Each of the 8 convolution filter kernels may be a block of 7 by 7 pixels along with 8 feature maps of 80 by 80 pixels apiece. The convolution layer 422 is followed by an activation function (non-linearities) 424 (e.g., Rectified Linear Unit or ReLU, such as $f(x)=\max(0,x)$) and max-pooling (feature pooling) 426 of 8 kernels in 4 by 4 pixel neighborhoods and subsampling with a stride of 4 pixels, resulting in 8 feature maps of 20 by 20 pixels each at the end of the first stage 420. Note that other activation functions such as sigmoid or tan h( ) may be used in other embodiments. In image classification applications, ReLU may help the network to converge quickly and with higher accuracy during training.

In the second stage 430, the convolution layer 432 may have 128 convolution filter kernels of 7 by 7 pixels each along with 32 feature maps of 14 by 14 pixels apiece, The convolution layer 432 is followed by an ReLU layer 434 and max-pooling 436 of 32 kernels in 2 by 2 pixel neighborhoods with subsampling, resulting in 32 feature maps of 7 by 7 pixels each at the end of the second stage 430.

In the third stage 440, the convolution layer 442 may have 2048 convolution filter kernels of 7 by 7 pixels each along with 128 feature maps of 1 by 1 pixels apiece (e.g., a 128-D vector), which is then fed to the Rectified Linear Unit layer (e.g., ReLU) 444. The Rectified Linear Unit 444 (see, e.g., Nair, Vinod, and Geoffrey E. Hinton. "Rectified Linear Units Improve Restricted Boltzmann Machines." *Proceedings of the 27th International Conference on Machine Learning (ICML-10).* 2010, the entire disclosure of which is incorporated herein by reference) is followed by a dropout module 446 (to reduce overfitting, such as too tight a correlation on the actual training images versus ability to properly classify non-training images) and a fully-connected linear NN classifier 448, which may produce K-class output, where K is the number of classes. For example, the NN classifier 448 may be a 6-neuron classifier (e.g., 6-output neuron classifier) configured to classify image images into one of six classes (e.g., one output neuron for each class).

To train a CNN, such as the CNN 400 illustrated in FIG. 4B above, for image classification, training images or data (such as training data 114 of FIG. 1) are used for each of the different classes that the classifier is intended to classify. See, for example, FIG. 3 and description below.

The CNN 400 may use the training data to develop a parametrized network or model (such as a classifier) that can discriminate among a set of classes. The model or classifier may benefit from a training set of images that contains samples representative of each class under a variety of conditions. This set may be collected, for example, by a human annotator (subject matter expert) who creates a reference dictionary of images representing a manual descriptive workflow.

The network (e.g., CNN 400) may learn from an arbitrary size of data (such as an arbitrary number of images of each class) as well as be extended to label an arbitrary number of classes. Note too, that the set may contain arbitrary sizes of images (e.g., different resolutions or aspect ratios) that, according to some of the embodiments of the present invention, may be fully exploited according to the data partitioning (e.g., preprocessing stage 410) scheme discussed above with reference to FIG. 2 (for example, converting each image to a consistent resolution, such as 86×86 pixels).

Figure 5:
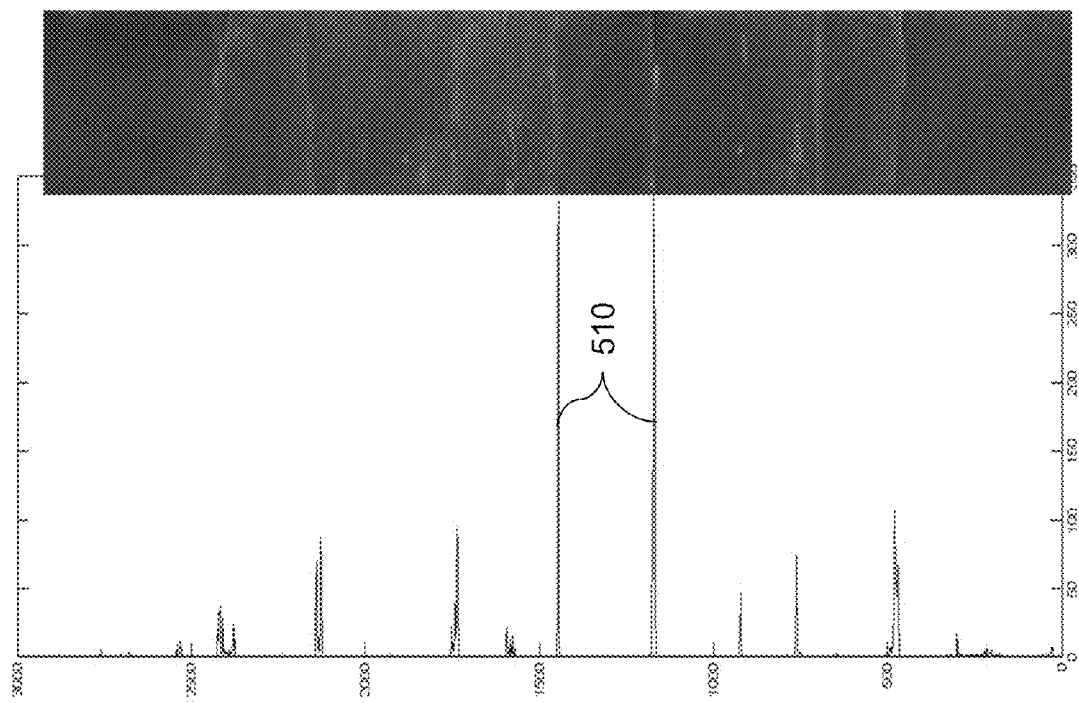
FIG. 5 illustrates an example sub-image extraction and crack detection approach using pixel intensities and integration to determine cracks according to an embodiment of the present invention.
Figure 6:
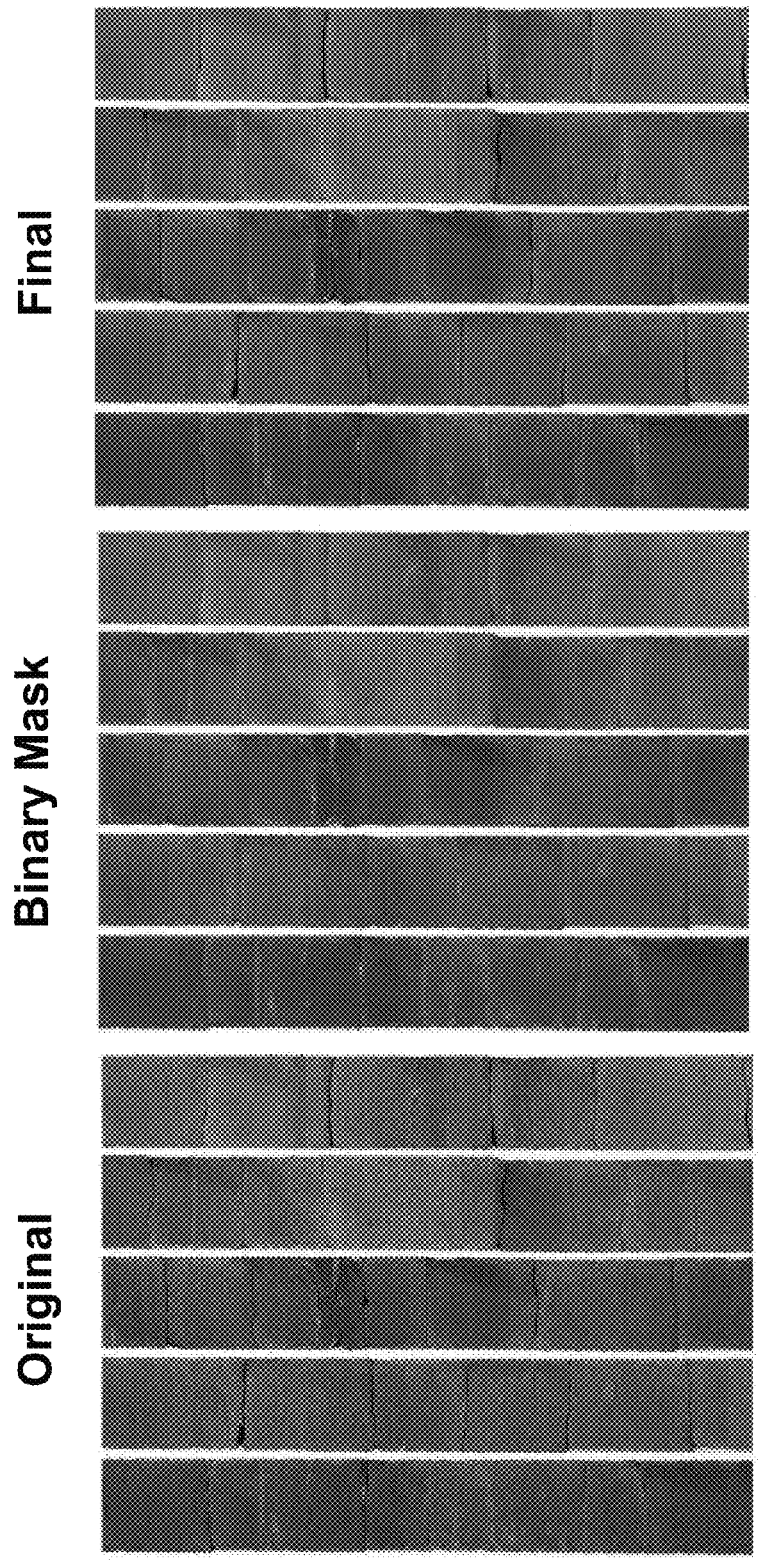
FIG. 6 illustrates example detected crack regions in partition images according to an embodiment of the present invention.

FIG. 5 illustrates an example sub-image extraction and crack detection approach using pixel intensities and integration to determine cracks according to an embodiment of the present invention. In the field of rock classifications cracks are darker (lower pixel value) than the rest of the sample and an indication of a crack type artifact may be generated by simply counting the number of pixel values less than a threshold at a particular depth. FIG. 6 illustrates example detected crack regions in partition images according to an embodiment of the present invention.

In FIG. 5, the y-axis represents pixel row or depth in the core sample and the x-axis represents the cumulative count of all pixels in that row in histogram format. In FIG. 6, three sets of five columns (two-foot columns, making up a 10-foot section) are shown, corresponding to original images (Original), images during crack detection (Binary Mask), and final images after crack detection (Final).

Referring to FIGS. 5-6, artifact detection (such as crack detection using an artifact detection scheme), may be performed on images to better prepare the images for classification before further steps (e.g., partitioning, sampling the partitions, etc.). This may detect artifacts in the image, for example, cracks, saw marks, voids, etc. For instance, in an embodiment of the present invention, horizontal thin cracks are searched for and detected as they may be the most widely occurring artifact. In other embodiments, cracks as well as other artifacts such as saw marks and voids may be detected using image processing methods that are applicable to that artifact, as would be apparent to one of ordinary skill in the art. In another embodiment, complex artifacts such as saw marks are treated and detected differently than cracks. When these types of artifacts are suspected, a 2-stage classifier is applied to the sub-images. First, referring to FIG. 3, the classifier is run by using a back-end classifier that is trained on 2-class artifact training data, where the two classes are: {<with-saw-marks>, <without-saw-marks>}. The sub-images that are classified as <with-saw-marks> during this classification stage are then removed from subsequent analysis of the standard second-stage rock image classification. The artifact back-end classifier can be extended to other types of complex artifacts as well (e.g., more than two classes).

According to one embodiment of the present invention, crack detection may be performed by thresholding the image (or partition) based on pixel intensities (see FIG. 5). For example, cracks may be much darker than the rest of the image and pixel values below a threshold value (e.g., a value of 10) may identify such pixels as sufficiently dark pixels. When the count of such pixels (i.e., count of pixels below the threshold value) in a horizontal band (row of the image) exceeds a threshold (e.g., 200), this may be reported as a detected crack.

See, for example, FIG. 5, which identifies two such cracks 510, and FIG. 6 (Binary Mask), which colors all such dark pixels a bright red (e.g., if and only if their pixel values are below the threshold value), the cracks then appearing visually as horizontal rows of bright red. The lower and upper row numbers of the pixels that define each of these cracks may then be identified. This analysis may be done for all partitions.

Each partition may then be sampled to generate N sub-images (or chips) of appropriate dimensions that depend, for example, on the classifier input size (e.g., N=20, where the classifier input size is 86×86 pixels each). However, these numbers may be adjusted in other embodiments depending on factors such as the expected classifier input size, partition size, desired confidence, etc., as would be apparent to one of ordinary skill in the art.

This sampling may produce sub images that are suitable for classification and capture information representative of the true class within the partition, but also allow generation of sufficient confidence scores (described below). Any sub-image that overlaps an artifact detected in the previous processing step may be handled appropriately, such as discarded. For ease of description, this process is depicted and described herein for a ten-foot core photo broken up into five vertical two-foot strips, as in the sample configurations shown in FIGS. 4A and 6, though the present invention is not limited thereto. In these examples, 10 vertical partitions may be used (in each column) and 20 sub images generated from each partition. Note that the width of the partition may be determined such that it fits within the core column (for example, the width may be the same as the height or depth of each partition), while (on average) avoiding voids in the core.

What follows are descriptions of three example methods for sub-image extraction according to embodiments of the present invention. Two of these methods may be extended to extracting an arbitrary N sample size for classification. As N increases, more of the true partition may be observed (e.g., the N sub images may cover a larger or more representative portion of the partition).

The first method attempts to discretize the partition to fit as many samples with dimension equal to the classifier input requirement (e.g., 86×86), such as with a uniform grid-like placement). While the partition is uniformly covered by a grid, the number of samples may be limited by the vertical partitioning of the core (e.g., partition size). This method may provide for sampling every portion of the partition (e.g., minimize the number of samples while providing complete coverage), but may also truncate features (such as dominant features) belonging to the lithofacies, which may lead to lower confidence scores or possibly even selecting a less dominant classification for the partition.

A second method, which alleviates some of these risks, is uniform random sampling of the partition. This may allow for an arbitrary N samples to be extracted that (when N is large) captures the true class of the partition. However, N may be significantly larger than with the first method (such as two times as many or more to enable, for example, all or most of the facet to be covered) and there may be no guarantee that features will be captured in their entirety.

A third, and preferred, method is uniform gridding with overlap to achieve maximum coverage of the partition as well as avoiding or minimizing truncating of features. The overlap may be chosen, for example, at 50% to ensure one of the sub-images captures the entire feature. This, however, may result in four times as many sub-images being selected (using 50% overlap as an example, with even more sub-images being selected for higher overlap amounts).

As part of the classification, each of the sub-images may be processed by the classifier and assigned a class label that corresponds to the maximum score class. The class of each partition may then be determined by majority voting of its sub-image classes. In one embodiment, the partition class confidence may be determined as the number of sub-images contributing to the majority class divided by the total number of sub-images in that partition. Other embodiments may use the class score of each of the classes from the sub-images of the partition to generate a partition class label and confidence from each of the represented classes (or those classes whose representation exceeds a set or predetermined threshold). Yet another embodiment may be to use the average of class probabilities from all of the sub-images, normalized to sum to 1.0.

Figure 7:
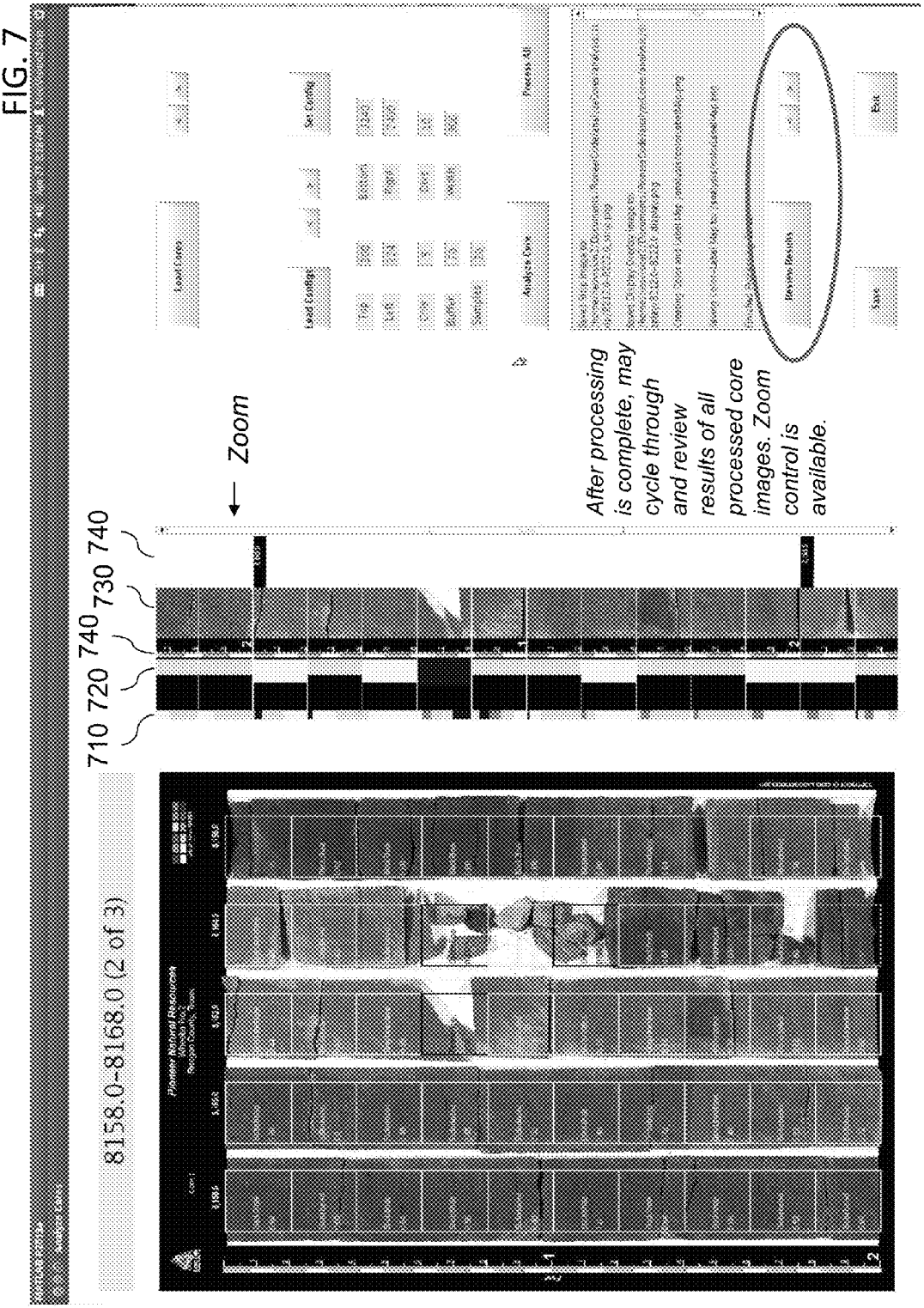
FIG. 7 illustrates an example classifier result visualization according to an embodiment of the present invention.

FIG. 7 illustrates an example classifier result visualization according to an embodiment of the present invention.

After processing is complete, may cycle through and review results of all processed core images. Zoom control is available. Referring to FIG. 7, an automated classification system according to an embodiment of the present invention may produce multiple types of results and easy visualizations, for example, overlaying of the classification results on the input core image, vertically concatenated image strips displaying confidence information graphically, and depth-aligned logs. As depicted in the left of FIG. 7, the original input core may be broken into partitions with their corresponding classifications and confidences overlaid, in the middle of FIG. 7 is an example strip image, and in the right of FIG. 7 are various configurations that can be changed or left alone for automatic processing as well as an update window for various stages of the core analysis system.

In FIG. 7 (left), core analysis graphical results show the original core image overlaid with color-coded partition delimiters, class labels, and confidence results. These may allow for quick inspection by a user, who in some embodiments may interactively modify the log (for example, to correct a mistake by the automated classifier).

FIG. 7 (middle) shows strip image results with three regions. In a strip image, a portion of the core (e.g., 10%, 20%, 25%), is visible, the exact amount being dependent on factors such as the magnification amount or zoom. The first (e.g., leftmost) region 710 in the strip image results may be a color-coded stack of bars whose proportion to the partition height depicts the confidence of each of the lithofacies (or rock strata) (e.g., the most prevalent class on the bottom, with further classes appearing in decreasing order of confidence), the second (e.g., middle) region 720 may be a bar whose width is proportional to the confidence and whose color is that of the majority label, and the third (e.g., rightmost) region 730 may be the actual partition of the core used for classification. The strip may also have the depth displayed 740 marking the start of each partition and section along the core. All of this information may be useful because any misclassification may be interactively corrected (e.g., by an analyst or other specialist) and saved so that, for example, future iterations of the classifier may be improved by training on samples it has never seen.

Table 1 is an example depth-aligned output log file from a core analysis according to an embodiment of the present invention.

TABLE 1

% Depth Amplitude
% Time of Log Save: 4 Aug. 2015 17:08:05
% Class Mapping Bioturbated: 1 BlackShale: 2 DebrisFlow: 3 HorizLaminated: 4 BuffSandstone: 5 GreyLimestone: 6
% Depth, Confidence Class 1, Confidence Class 2, Confidence Class 3, Confidence Class 4, Confidence Class 5, Confidence Class 6

| Depth | C1 | C2 | C3 | C4 | C5 | C6 |
|---|---|---|---|---|---|---|
| 7980.0, | 0.60, | 0.00, | 0.05, | 0.35, | 0.00, | 0.00 |
| 7980.5, | 0.57, | 0.00, | 0.00, | 0.25, | 0.00, | 0.17 |
| 7981.0, | 0.25, | 0.03, | 0.00, | 0.55, | 0.00, | 0.17 |
| 7981.5, | 0.10, | 0.72, | 0.03, | 0.15, | 0.00, | 0.00 |
| 7982.0, | 0.53, | 0.05, | 0.00, | 0.42, | 0.00, | 0.00 |
| 7982.5, | 0.28, | 0.03, | 0.00, | 0.70, | 0.00, | 0.00 |
| 7983.0, | 0.35, | 0.35, | 0.00, | 0.23, | 0.00, | 0.07 |
| 7983.5, | 0.50, | 0.05, | 0.03, | 0.38, | 0.00, | 0.05 |
| 7984.0, | 0.35, | 0.28, | 0.00, | 0.35, | 0.00, | 0.03 |
| 7984.5, | 0.05, | 0.62, | 0.00, | 0.30, | 0.00, | 0.03 |
| 7985.0, | 0.35, | 0.15, | 0.00, | 0.15, | 0.00, | 0.35 |
| 7985.5, | 0.45, | 0.00, | 0.00, | 0.25, | 0.00, | 0.30 |
| 7986.0, | 0.25, | 0.03, | 0.00, | 0.17, | 0.00, | 0.55 |
| 7986.5, | 0.23, | 0.42, | 0.00, | 0.23, | 0.00, | 0.12 |
| 7987.0, | 0.10, | 0.65, | 0.00, | 0.17, | 0.00, | 0.07 |
| 7987.5, | 0.05, | 0.17, | 0.00, | 0.78, | 0.00, | 0.00 |
| 7988.0, | 0.05, | 0.28, | 0.00, | 0.35, | 0.07, | 0.25 |
| 7988.5, | 0.28, | 0.05, | 0.00, | 0.17, | 0.00, | 0.50 |
| 7989.0, | 0.10, | 0.45, | 0.00, | 0.28, | 0.05, | 0.12 |
| 7989.5, | 0.23, | 0.28, | 0.00, | 0.38, | 0.00, | 0.12 |
| 7990.0, | 0.72, | 0.00, | 0.00, | 0.28, | 0.00, | 0.00 |

. . . .

Figure 8:
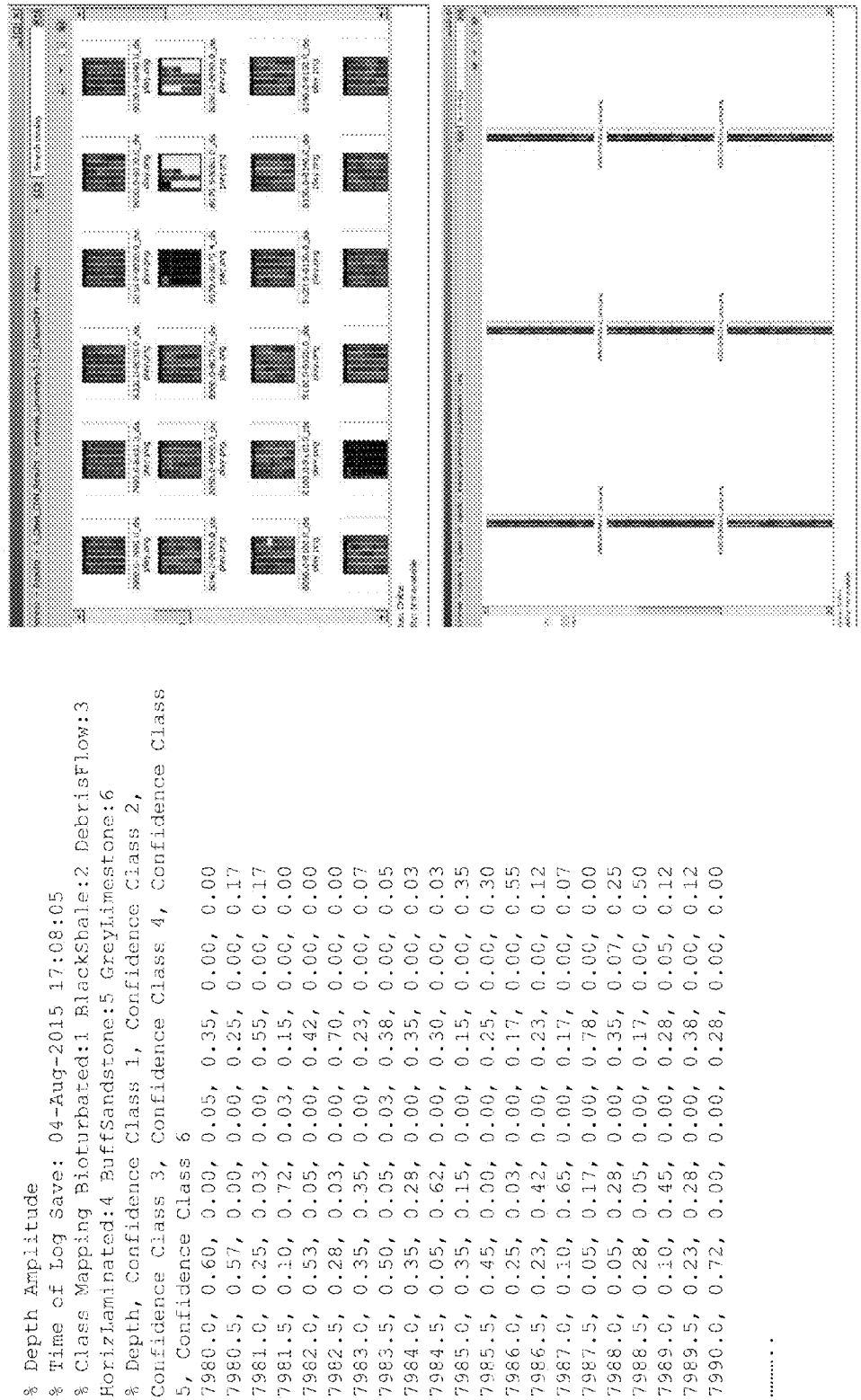
FIG. 8 is an example of images associated with a depth-aligned output log file from a core analysis according to an embodiment of the present invention.

Table 1 shows the depth-aligned log file that is a comma separated value (CSV) file containing the classification results of each of the partitions. Each line in the log file may contain the depth of the partition, its classification, its confidence, and, if the user desires, the confidence of all other lithofacies. FIG. 8 shows image corresponding to lines of the depth-aligned log file. Note that in an embodiment of the present invention, the core analysis tool may process and complete classification of one core photo in a few seconds on a standard laptop computer with an interpretive fidelity at parity to human description.

Figure 9:
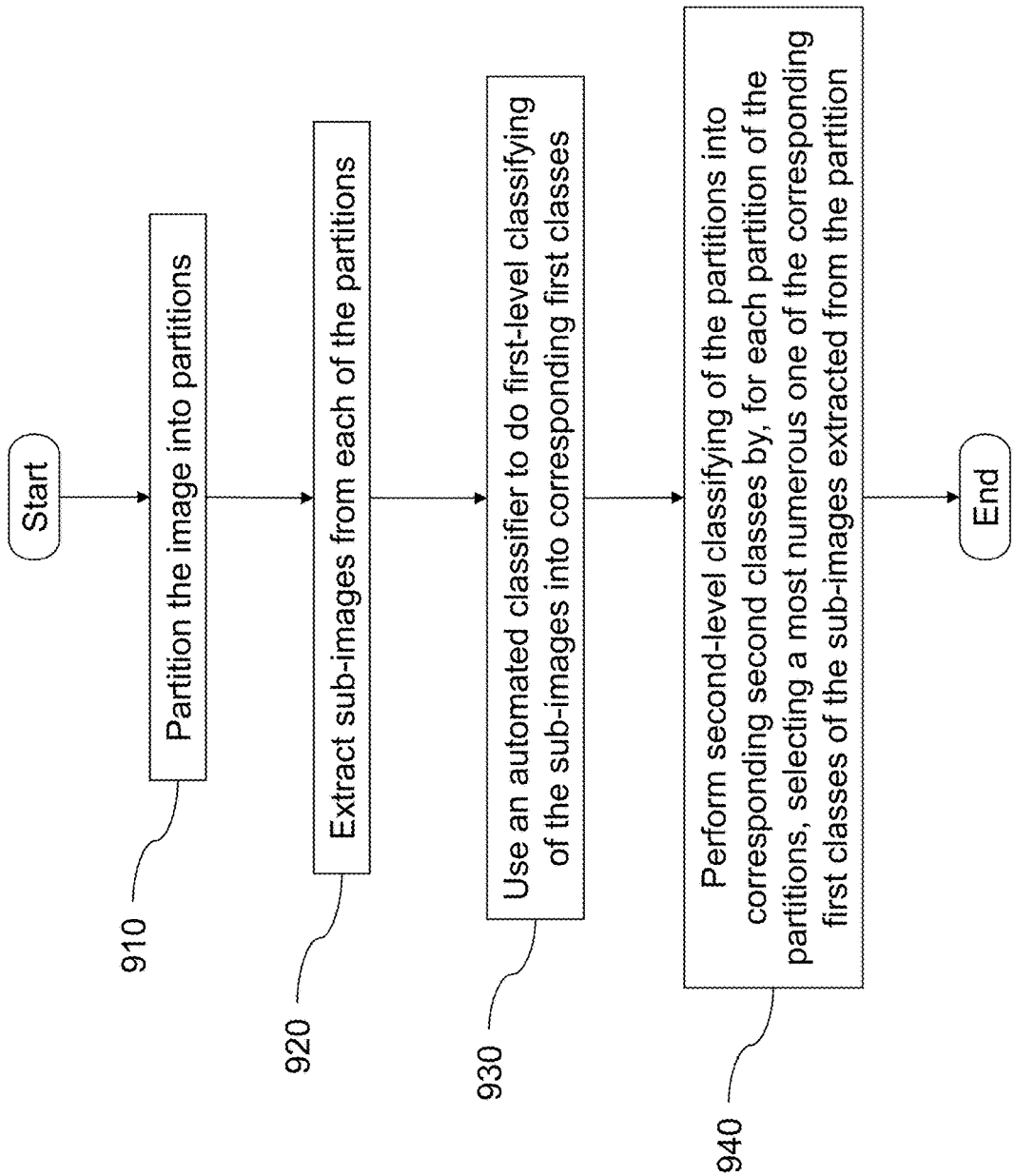
FIG. 9 is a flow diagram of an example method for automated classification of an image according to an embodiment of the present invention.

FIG. 9 is a flow diagram of an example method for automated classification (for example, on a processing device or computing system implementing the Core Classification System—Front End 120) of an image according to an embodiment of the present invention.

In the method of FIG. 9, processing begins, and in step 910, the image is partitioned (e.g., divided) into partitions. In step 920, sub-images (e.g., chips) are extracted from each of the partitions. In step 930, an automated classifier is used to do first-level classifying of the sub-images into corresponding first classes. In step 940, second-level classifying of the partitions into corresponding second classes is performed by, for each partition of the partitions, selecting a most numerous one of the corresponding first classes of the sub-images extracted from the partition.

The above and other methods disclosed herein may be implemented, for example, as a series of computer instructions to be executed by a processor (or other computing device), such as a microprocessor, or two or more processors. The processor(s) may execute computer program instructions and interact with other system components for performing the various functionalities described herein. The computer program instructions may be stored in a memory implemented using a standard memory device, such as, for example, a random access memory (RAM). The computer program instructions may also be stored in other non-transitory computer readable media such as, for example, a CD-ROM, flash drive, or the like. The methods may also be implemented using hardware circuits (e.g., transistors, capacitors, logic gates, FPGAs, etc.), or combinations of hardware circuits, software, and firmware, as would be apparent to one of ordinary skill.

Figure 10:
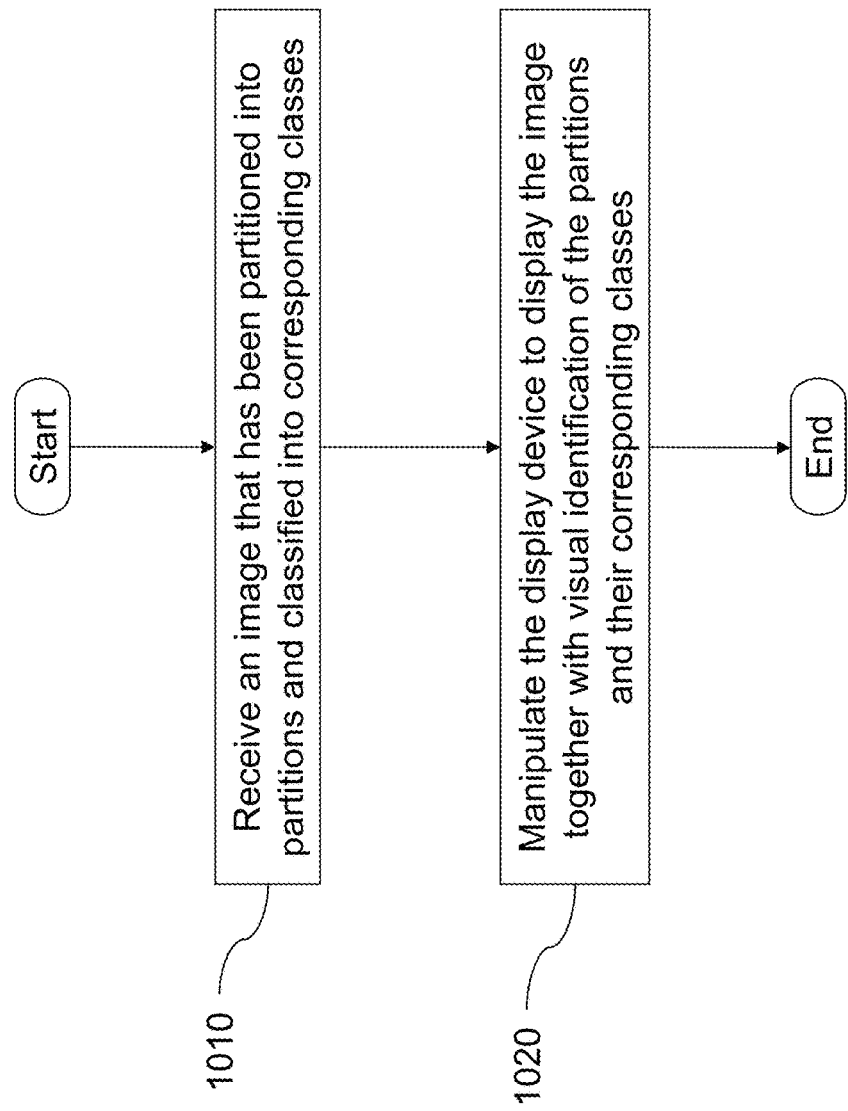
FIG. 10 is a flow diagram of an example method of displaying automated classification results of an image on a display device according to an embodiment of the present invention.

FIG. 10 is a flow diagram of an example method of displaying automated classification results (for example, by a computer processor) of an image on a display device according to an embodiment of the present invention.

In the method of FIG. 10, processing begins, and in step 1010, an image is received, the image being partitioned into partitions and classified into corresponding classes (for example, by the method of FIG. 9). In step 1020, the display device is manipulated (for example, by the computer processor) to display the image together with visual identification of the partitions and their corresponding classes.

Figure 11:
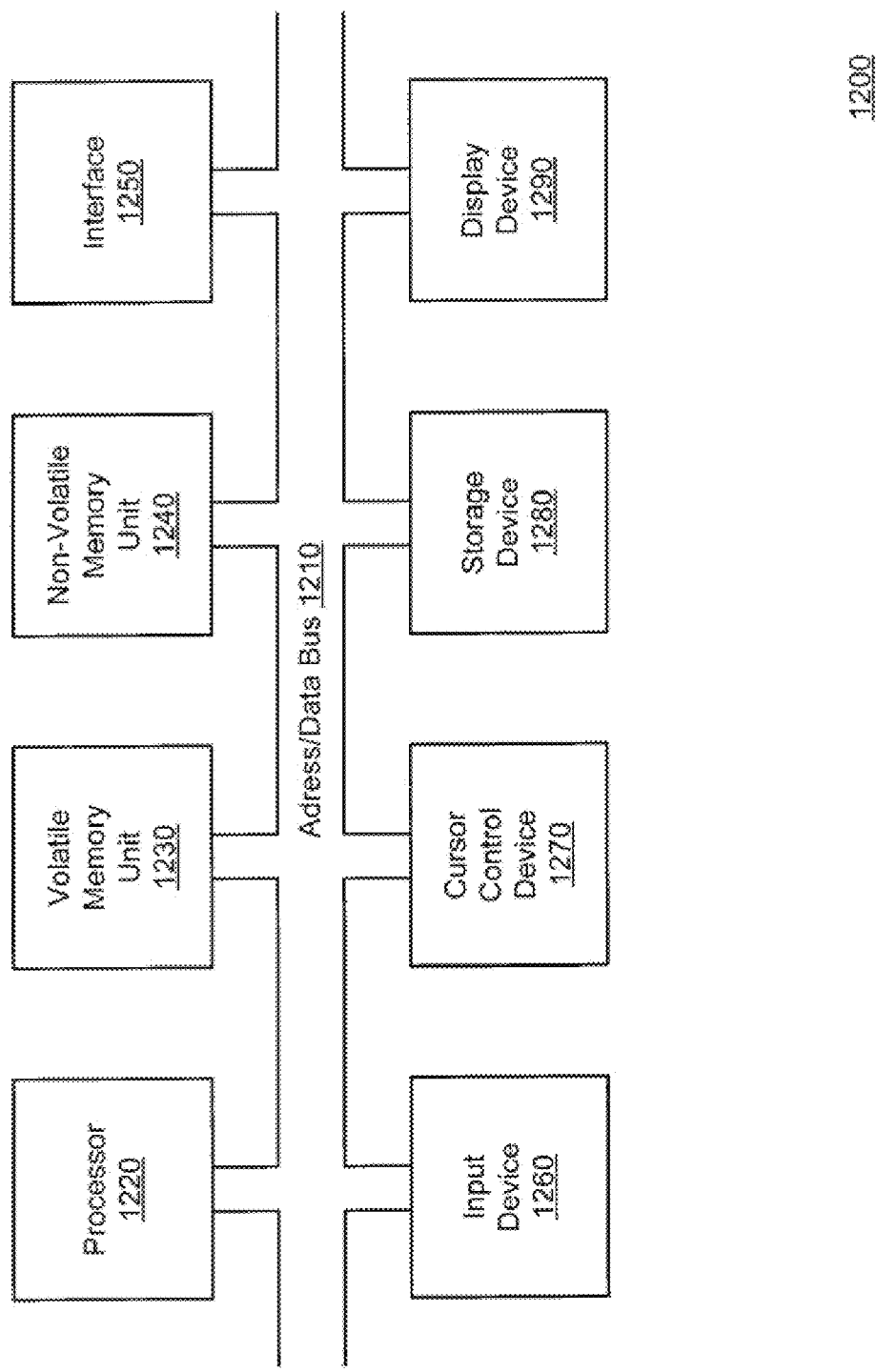
FIG. 11 is a block diagram of a computer system in accordance with one embodiment of the present invention.

An exemplary computer system 1200 in accordance with an embodiment is shown in FIG. 11. Exemplary computer system 1200 is configured to perform calculations, processes, operations, and/or functions associated with a program or algorithm. In one embodiment, certain processes and steps discussed herein are realized as a series of instructions (e.g., software program) that reside within computer readable memory units and are executed by one or more processors of exemplary computer system 1200. When executed, the instructions cause exemplary computer system 1200 to perform specific actions and exhibit specific behavior, such as described herein.

Exemplary computer system 1200 may include an address/data bus 1210 that is configured to communicate information. Additionally, one or more data processing unit, such as processor (or CPU) 1220, are coupled with address/data bus 1210. Processor 1220 is configured to process information and instructions. In an embodiment, processor 1220 is a microprocessor. Alternatively, processor 1220 may be a different type of processor such as a parallel processor, or a field programmable gate array.

Exemplary computer system 1200 is configured to utilize one or more data storage units. Exemplary computer system 1200 may include a volatile memory unit 1230 (e.g., random access memory ("RAM"), static RAM, dynamic RAM, etc.) coupled with address/data bus 1210, wherein volatile memory unit 1230 is configured to store information and instructions for processor 1220. Exemplary computer system 1200 further may include a non-volatile memory unit 1240 (e.g., read-only memory ("ROM"), programmable ROM ("PROM"), erasable programmable ROM ("EPROM"), electrically erasable programmable ROM "EEPROM"), flash memory, etc.) coupled with address/data bus 1210, wherein non-volatile memory unit 1240 is configured to store static information and instructions for processor 1220. Alternatively exemplary computer system 1200 may execute instructions retrieved from an online data storage unit such as in "Cloud" computing. In an embodiment, exemplary computer system 1200 also may include one or more interfaces, such as interface 1250, coupled with address/data bus 1210. The one or more interfaces are configured to enable exemplary computer system 1200 to interface with other electronic devices and computer systems. The communication interfaces implemented by the one or more interfaces may include wireline (e.g., serial cables, modems, network adaptors, etc.) and/or wireless (e.g., wireless modems, wireless network adaptors, etc.) communication technology.

In one embodiment, exemplar computer system 1200 may include an input device 1260 coupled with address/data bus 1210, wherein input device 1260 is configured to communicate information and command selections to processor 1220. In accordance with one embodiment, input device 1260 is an alphanumeric input device, such as a keyboard, that may include alphanumeric and/or function keys. Alternatively, input device 1260 may be an input device other than an alphanumeric input device. In an embodiment, exemplar computer system 1200 may include a cursor control device 1270 coupled with address/data bus 1210, wherein cursor control device 1270 is configured to communicate user input information and/or command selections to processor 1220. In an embodiment, cursor control device 1270 is implemented using a device such as a mouse, a track-ball, a track-pad, an optical tracking device, or a touch screen. The foregoing notwithstanding, in an embodiment, cursor control device 1270 is directed and/or activated via input from input device 1260, such as in response to the use of special keys and key sequence commands associated with input device 1260. In an alternative embodiment, cursor control device 1270 is configured to be directed or guided by voice commands.

Figure 12:
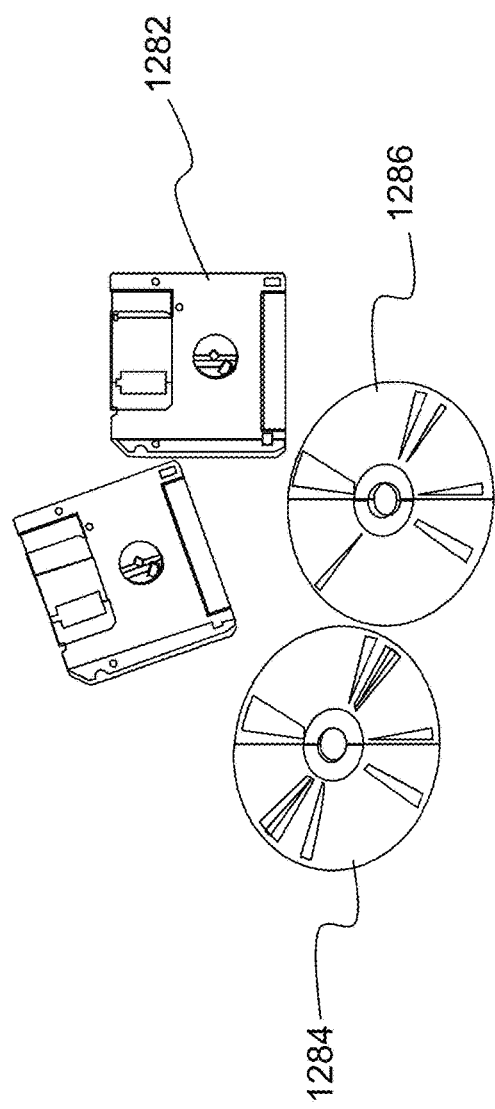
FIG. 12 depicts examples of non-volatile media that may be used with a storage device according to embodiments of the present invention.

In an embodiment, exemplary computer system 1200 further may include one or more optional computer usable data storage devices, such as storage device 1280, coupled with address/data bus 1210. Storage device 1280 is configured to store information and/or computer executable instructions. FIG. 12 depicts examples of non-volatile media that may be used with a storage device according to embodiments of the present invention. In one embodiment, storage device 1280 is a storage device such as a magnetic or optical disk drive (e.g., hard disk drive ("HDD"), floppy diskette 1282, compact disk read only memory ("CD-ROM") 1284, or digital versatile disk ("DVD") 1286). Pursuant to one embodiment, a display device 1290 is coupled with address/data bus 1210, wherein display device 1290 is configured to display video and/or graphics. In an embodiment, display device 1290 may include a cathode ray tube ("CRT"), liquid crystal display ("LCD"), field emission display ("FED"), plasma display or any other display device suitable for displaying video and/or graphic images and alphanumeric characters recognizable to a user.

Exemplary computer system 1200 is presented herein as an exemplary computing environment in accordance with an embodiment. However, exemplary computer system 1200 is not strictly limited to being a computer system. For example, an embodiment provides that exemplary computer system 1200 represents a type of data processing analysis that may be used in accordance with various embodiments described herein. Moreover, other computing systems may also be implemented. Indeed, the spirit and scope of the present technology is not limited to any single data processing environment. Thus, in an embodiment, one or more operations of various embodiments of the present technology are controlled or implemented using computer-executable instructions, such as program modules, being executed by a computer. In one exemplary implementation, such program modules include routines, programs, objects, components and/or data structures that are configured to perform particular tasks or implement particular abstract data types. In addition, an embodiment provides that one or more aspects of the present technology are implemented by utilizing one or more distributed computing environments, such as where tasks are performed by remote processing devices that are linked through a communications network, or such as where various program modules are located in both local and remote computer-storage media including memory-storage devices.

Core analysis utilization of the classifier-based technology in the present application unequivocally demonstrates that once trained with a task-specific dictionary, the application may deliver descriptive results parallel to the efficacy of a subject matter expert. The success of these simple, yet very rigorous, trials of embodiments of the present invention foreshadows extensive applications within the niche of descriptive geoscience, a highly observation-based science that drives our upstream energy sector. In other ongoing embodiments, early results from trials that merge the image analysis dictionaries with the quantitative proxies from sub-surface petrophysics suggest a broad spectrum of potential applications heretofore unrealized within the upstream energy sector.

While the present invention has been described in connection with certain example embodiments, it is to be understood that the invention is not limited to the disclosed embodiments, but, on the contrary, is intended to cover various modifications and equivalent arrangements.

What is claimed is:

1. A method of automated classification comprising:
    partitioning, by a Core Classification System—Front End, an image into partitions;
    extracting, by the Core Classification System—Front End, sub-images from each of the partitions, a plurality of sub-images associated with each partition of the partitions being extracted from different portions of the partition;
    first-level classifying, by an automated classifier, the sub-images into corresponding first classes; and
    second-level classifying, by the Core Classification System—Front End, the partitions into corresponding second classes by, for each partition of the partitions, selecting a most numerous one of the corresponding first classes of the sub-images extracted from the partition.

2. The method of claim 1, further comprising displaying, on a display device, visual results of the automated classification, the visual results comprising the image together with visual identification of the partitions and their corresponding second classes.

3. The method of claim 1, wherein the image is of a rock core sample, the partitions are of different portions of the core sample, and each of the first and second classes identify different rock strata.

4. The method of claim 3, further comprising displaying, on a display device, visual results of the automated classification, the visual results comprising the image together with visual identification of the partitions and their corresponding second classes distinguishing the different rock strata.

5. The method of claim 3, further comprising identifying, by the Core Classification System—Front End, one or more artifacts in the partitions, wherein the extracting of the sub-images comprises excluding any of the sub-images that contain any of the artifacts.

6. The method of claim 1, wherein the automated classifier is a convolutional neural network within the Core Classification System—Front End.

7. The method of claim 1, wherein the partitioning of the image comprises dividing the image into nonoverlapping said partitions.

8. The method of claim 1, wherein the selecting of the most numerous one of the corresponding first classes of the sub-images extracted from the partition further comprises assigning a confidence score to the selection based on a distribution of the corresponding first classes of the sub-images extracted from the partition.

9. The method of claim 8, further comprising displaying, on a display device, visual results of the automated classification, the visual results comprising the image together with visual identification of the partitions and their corresponding second classes and confidence scores.

10. A system for automated classification, comprising:
a central processing unit;
an automated classifier; and
a non-transitory physical medium, wherein the medium has instructions stored thereon that, when executed by the central processing unit, causes the central processing unit to:
partition an image into partitions;
extract sub-images from each of the partitions, a plurality of sub-images associated with each partition of the partitions being extracted from different portions of the partition;
perform first-level classification of the sub-images into corresponding first classes using the automated classifier; and
perform second-level classifying of the partitions into corresponding second classes by, for each partition of the partitions, selecting a most numerous one of the corresponding first classes of the sub-images extracted from the partition.

11. The system of claim 10, wherein the automated classifier is configured to run on the central processing unit.

12. The system of claim 10, wherein the automated classifier is configured to run on a neuromorphic chip.

13. The system of claim 10, wherein the medium further has instructions stored thereon that, when executed by the central processing unit, cause the central processing unit to:
identify one or more artifacts in the partitions,
wherein the instructions that, when executed by the central processing unit, cause the central processing unit to extract the sub-images from each of the partitions comprise instructions that cause the central processing unit to exclude any of the sub-images that contain any of the artifacts.

14. The system of claim 10, wherein the medium further has instructions stored thereon that, when executed by the central processing unit, causes the central processing unit to:
display, on a display device, visual results of the classification, the visual results comprising the image together with visual identification of the partitions and their corresponding second classes.

15. A non-volatile computer readable medium having instructions stored thereon that, when executed by a central processing unit, cause the central processing unit to:
receive an image;
partition the image into a plurality of partitions;
extract sub-images from each of the partitions, a plurality of sub-images associated with each partition of the partitions being extracted from different portions of the partition;
first-level classify, by an automated classifier, the sub-images into corresponding first classes; and
second-level classify the partitions into second classes by, for each partition of the partitions, selecting a most numerous one of the corresponding first classes of the sub-images extracted from the partition.

16. The non-volatile computer readable medium of claim 15, further having instructions stored thereon that, when executed by the central processing unit, cause the central processing unit to display, on a display device, visual results of the automated classification, the visual results comprising the image together with visual identification of the partitions and their corresponding second classes.

17. The non-volatile computer readable medium of claim 15, wherein the image is of a rock core sample, the partitions are of different portions of the core sample, and each of the first and second classes identify different rock strata.

* * * * *